United States Patent
Berggren et al.

(10) Patent No.: US 6,586,188 B1
(45) Date of Patent: Jul. 1, 2003

(54) METHOD FOR IDENTIFICATION OF COMPOUNDS THAT BIND TO β-TUBULIN AND STIMULATE INSULIN SECRETION

(75) Inventors: Per-Olof Berggren, Stockholm (SE); Thomas Lundbäck, Enskededalen (SE); Alejandro Bertorello, Stockholm (SE)

(73) Assignee: Biovitrum AB, Stockholm (SE)

( * ) Notice: Subject to any disclaimer, the term of this patent is extended or adjusted under 35 U.S.C. 154(b) by 0 days.

(21) Appl. No.: 09/637,134

(22) Filed: Aug. 11, 2000

Related U.S. Application Data
(60) Provisional application No. 60/150,098, filed on Aug. 20, 1999.

(30) Foreign Application Priority Data
Aug. 13, 1999 (SE) .................................................. 9902918

(51) Int. Cl.⁷ ........................ G01N 33/53; G01N 33/567
(52) U.S. Cl. ..................... 435/7.1; 435/72; 435/7.21; 436/501
(58) Field of Search ..................... 435/7.1, 7.2, 7.21; 436/501; 514/1

(56) References Cited

PUBLICATIONS

P.R. Flatt, O.Shiber, J. Szecowka and Per–Olof Berggren; "New Perspectives On The Actions of Sulphony Lureas and Hyperglycaemic Sulphonamides On The Pancreatic β–Cell," *Diabetes & Metabolisme* (Paris), 1994, 20, 157–162.

L. Luzi and G. Pozza, "Glibenclamide": an old drug with a novel mechanism of action?, *Aeta Diabetol*, 34:239–244.

Lena Eliasson, Erik Renström, Carina Ämmälä, Per–Olof Berggren, Alejandro M. Bertorello, Krister Bokuist, Alexander Chibalin, Jude T. Deeney, Peter R. Flatt, Jakob Gäbel, Jesper Gromada, Olof Larsson, Per Lindström, Christopher J. Rhodes and Patrik Rorsman, "PKC–Dependent Stimulation of Exocytosis by Sulfonylureas in Pancreatic β Cells," *Science*, vol. 271, pp. 83–815, Feb. 9, 1996.

Ya–Min Tian, Gabriele Johnson and J.H. Stephen, "Sulfanylureas Enhance Exocytosis From Pancreatic beta–cells by a Mechanism That Does Not Involve Direct Activation of Protein Kinase C," *Diabetes*, vol. 47(II), pp. 1722–1726, Nov. 1998.

Sebastian Barg, Erik Renström, Per–Olof Berggren, Alejandro Bertorello, Krister Bokvist, Matthias Braun, Lena Eliasson, William E. Holmes, Martin Köhler, Patrik Rorsman and Frank Thevenod, "The Stimulatory Action of Tolbutamide on $Ca^{2+}$–dependent Exocytosis in Pancreatic β Cells is Mediated by a 65–kDa mdr–like P–glycoprotein," *Proc. Natl. Acad. Sci. USA*, vol. 96, pp. 5539–5544, May 1999.

*Primary Examiner*—Elizabeth Kemmerer
*Assistant Examiner*—Ruixiang Li
(74) *Attorney, Agent, or Firm*—Fish & Richardson P.C.

(57) ABSTRACT

According to the invention β-tubulin, as well as a 65 kDa polypeptide present in pancreatic β-cells, have been identified as molecular targets for sulfonylurea compounds. These findings enable for the identification of new insulin secretagogues. The invention thus relates to the use of sulfonylurea compounds, such as e.g. glibenclamide, in methods for identification of compounds binding the 65 kDa polypeptide or tubulin, or stimulating tubulin polymerization and/or turnover, thereby stimulating insulin secretion.

21 Claims, 3 Drawing Sheets

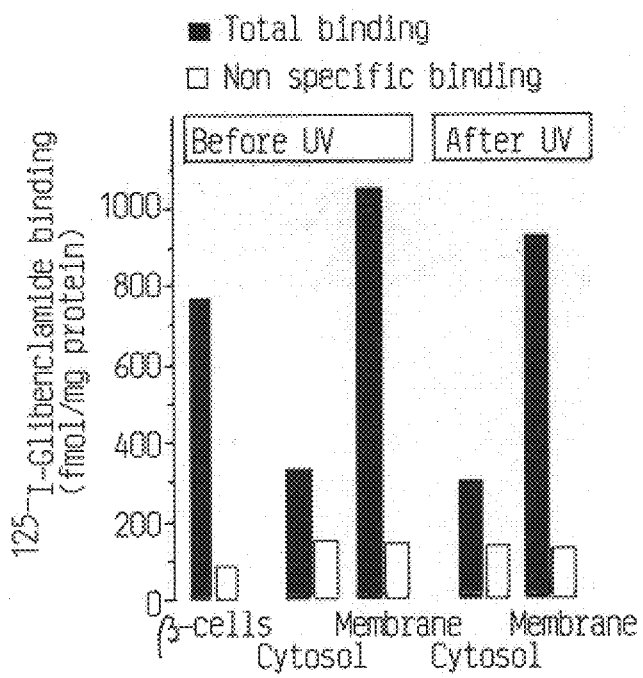
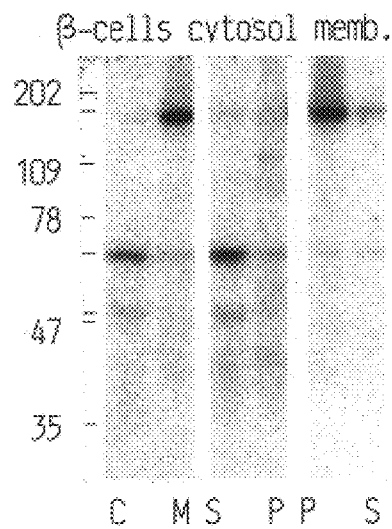
FIG. 1A  FIG. 1B
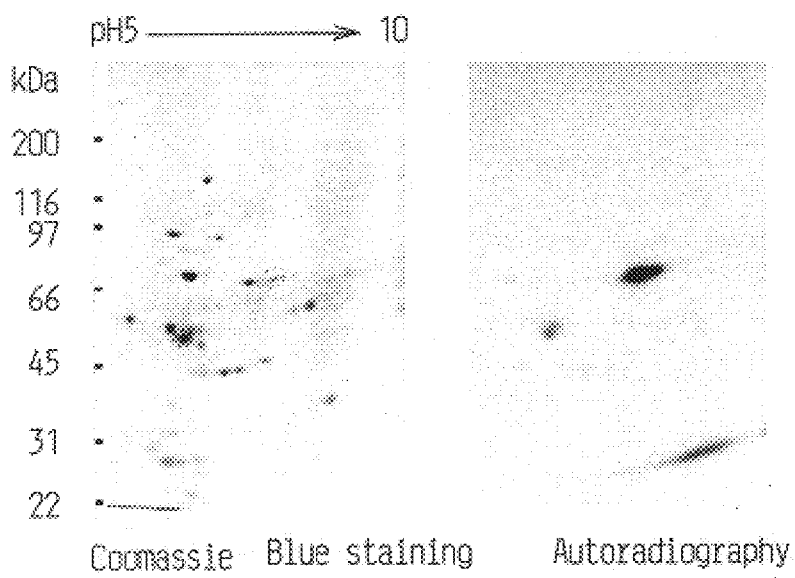
FIG. 1C

METHOD FOR IDENTIFICATION OF COMPOUNDS THAT BIND TO β-TUBULIN AND STIMULATE INSULIN SECRETION

CROSS REFERENCE TO RELATED APPLICATIONS

This application claims priority from Swedish Patent Application No. 9902918-3, filed Aug. 13, 1999, and U.S. Provisional Patent Application Serial No. 60/150,098, filed Aug. 20, 1999. These applications are incorporated herein by reference in their entirety.

TECHNICAL FIELD

According to the invention P-tubulin., as well as a new polypeptide present in pancreatic β-cells, have been identified as molecular targets for sulfonylurea compounds. These findings enable for the identification of new insulin secretagogues. The invention thus relates to the use of sulfonylurea compounds, such as e.g. glibenclamide, in methods for identification of compounds binding the new polypeptide or tubulin, or stimulating tubulin polymerization and/or turnover, said compounds thereby stimulating insulin secretion.

BACKGROUND ART

Diabetes mellitus is a chronic disease affecting approximately 3–5% of the Swedish population and it is associated with a variety of severe late complications leading to enhanced morbidity and mortality. Thus, this disease markedly compromises the health and life quality of affected individuals and consumes.a substantial amount of the health care budget.

Hyperglycemia is a major risk factor for the development of the specific diabetes-associated complications and probably also for the increased risk of cardiovascular disease. Early intervention, which requires diagnosis in the prediabetic state, is expected to contribute to a reduction of the diabetic complications. Hence, there is an urgent need for precise methods in the early detection of individuals at risk for the development of diabetes. Furthermore, there is a need for the design of new concepts and drugs for prevention and treatment of diabetes. A better understanding of the biochemical, cellular, genetic and molecular basis for the development of hyperglycemia and the effect of hyperglycemia on both release and action of insulin will pave the way for new drugs and future development of gene therapy in the treatment of diabetes. A defective insulin release is a characteristic of non-insulin dependent diabetes mellitus (NIDDM) and to some extent also to the early phase of insulin-dependent diabetes mellitus (IDDM).

An initial step in the β-cell stimulus-secretion coupling is metabolism of glucose, resulting in the formation of ATP. ATP closes the ATP-regulated $K^+$-channels ($K_{ATP}$ channels), resulting in plasma membrane depolarization, opening of voltage-gated L-type $Ca^{2+}$-channels and increase in cytoplasmic free $Ca^{2+}$ concentration, $[Ca^{2+}]i$. The $K_{ATP}$ channel is composed of at least two components: a sulfonylurea receptor (SUR) and an inward rectifier potassium channel protein (Aguilar-Bryan, L. et al. (1995) Science 268: 423–426). The binding of sulfonylureas (SU) to SUR1, the β-cell variant of SUR, results in the closure of the $K_{ATP}$ channels and thereby insulin release in the β-cell. Sulfonylurea compounds, such as glibenclamide (glyburide; 5-Chloro-N-[2-[4-[[[(cyclohexylamino) carbonyl]amino] sulfonyl]phenyl]ethyl]-2-methoxybenzamide, CAS: [10238-21-8]) have been used in the treatment of NIDDM (for a review, see Luzi, L. & Pozza, G. (1997) Acta Diabetol. 34, 239–244).

Sulfonylurea compounds are capable of promoting insulin secretion even in the absence of changes in membrane potential and intracellular calcium. It has been shown that sulfonylurea compounds directly promote exocytosis of insulin (Eliasson L. et al. (1996) Science 271: 813–815; Flatt et al. (1994) Diabete et Metabolisme 20: 157–162). This effect is dependent on protein kinase C and is observed at therapeutic concentrations of sulfonylureas, which suggests that it contributes to their hypoglycemic action in diabetics. It has been suggested that 80–90% of the SU binding proteins is localized to intracellular membranes, including those of the secretory granules (Ozanne S. E. et al. (1995) Diabetologia 38, 277–282). The molecular mechanism underlying this direct effect of sulfonylureas on insulin exocytosis is not known.

Consequently, there is a need for identification of new intracellular targets that could explain the effect of sulfonylureas on insulin exocytosis via a pathway independent of the sulfonylurea receptor (SUR-1) and the ATP-regulated $K^+$-channel. Such targets could be utilized in methods for the identification of new compounds stimulating insulin secretion.

The involvement of the microtubular network in glucose-induced insulin secretion has been suggested (Lacy, P. E. et al. (1968) Nature 219, 1177–1179). The hypothesis was based on the decreased insulin secretion observed in the presence of drugs that inhibit polymerization of the tubulin heterodimer to form microtubules. Subsequent studies revealed that the reduced secretion was observed both in the presence of microtubule stabilizers (e.g. $D_2O$ and ethanol) and destabilizers (e.g. colchicine and vincristine) (Malaisse, W. J. et al. (1970) Diabetologia 6, 683; Malaisse, W. J. et al. (1971) Diabetes 20, 257–265). It was also shown that the observed effect did not result from an altered insulin production or calcium uptake, demonstrating that it was the transport and/or secretion of insulin containing granules that was not functional. Following these results a model of insulin secretion was presented in which the second sustained phase of secretion depends on the directional transport of insulin granules along the microtubular network (Malaisse, W. J. et al. (1974) Eur. J. Clin. Invest. 4, 313–318).

A number of reports have since confirmed the importance of the microtubular system in insulin secretion (for a review, see Howell, S. L. & Tyhurst, M. (1986) Diabetes/ Metabolism Reviews, 2, 107–123). These studies revealed that the integrity and/or the dynamic equilibrium (treadmilling as well as phases of microtubule growth and shortening) of the microtubules are essential for glucose-stimulated insulin secretion. Of interest from a pharmaceutical viewpoint is to identify agents that act on the microtubule network to specifically enhance insulin secretion. This task is not trivial as the microtubular network is generally involved in secretory processes in several endocrine organs and glands (see e.g. Poisner, A. M. & Bernstein, J. (1971) J. Pharmacol. Exp. Ther. 177, 102–108; Neve, P. et al. (1970) Exp. Cell Res. 63, 457–460; Williams, J. A. & Wolff, J. (1970) Proc. Natl. Acad. Sci. U.S.A. 67, 1901–1908; Kraicer, J. & Milligan, J. V. (1971) Endocrinology 89, 408–412) and hence not expected to be a suitable target for a specific insulin secretagogue.

BRIEF DESCRIPTION OF THE DRAWINGS

FIGS. 1A, 1B, and 1C

Binding of [$^{125}$I]glibenclamide to pancreatic β-cells. (A) Binding of glibenclamide was examined in intact β-cells and subcellular fractions (cytosol and membranes) derived therefrom. Cross-linking (UV) did not affect the magnitude of the binding. (B) The cross-linked samples were further analyzed by SDS-PAGE and autoradiography (C, cytosol and M, membranes). These fractions were washed extensively, centrifuged and the supernatant (S) and pellets (P) further analyzed by SDS-PAGE and autoradiography. (C) The cytosolic fraction was further analyzed by 2-dimensional electrophoresis and autoradiography.

Figure 2A:
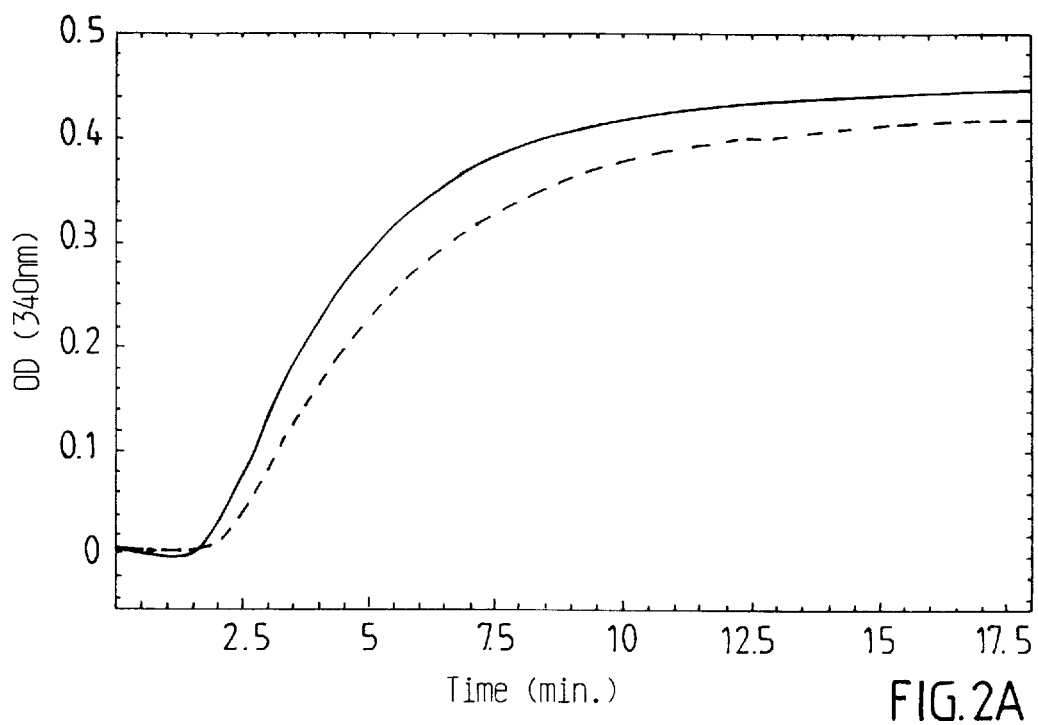
Figure 2B:
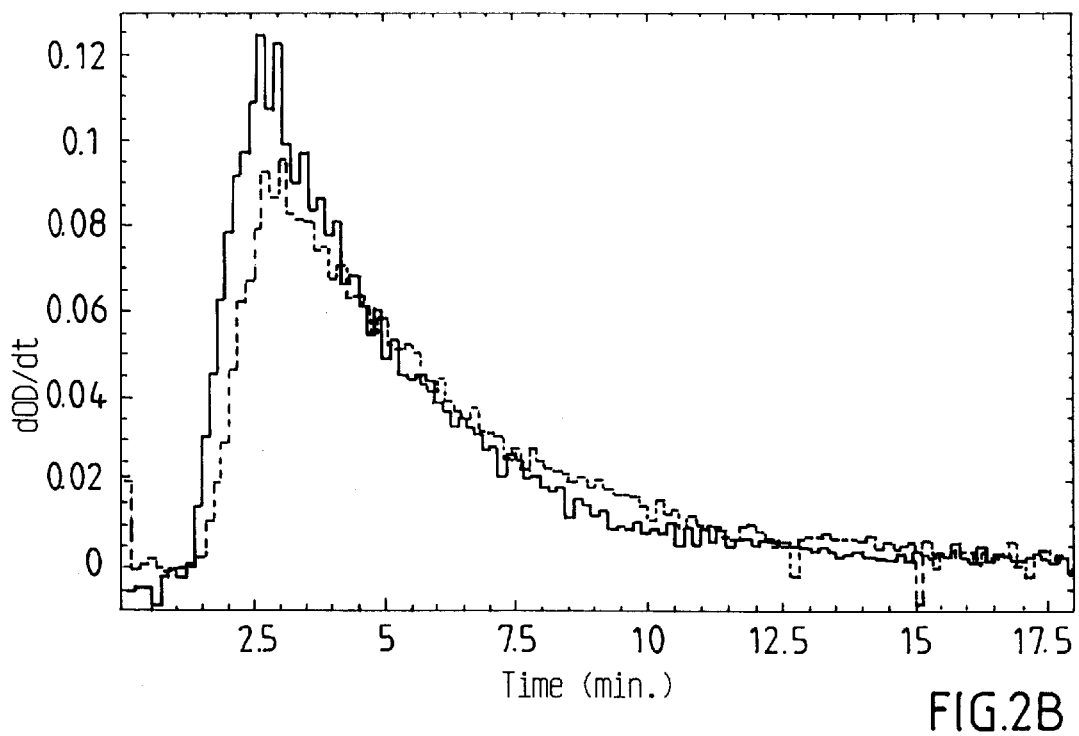

FIGS. 2A and 2B

Glibenclamide accelerates microtubule growth. (a): Experimental data showing the increase in optical density at 340 nm, resulting from tubulin polymerization in vitro, as a function of time. Microtubule growth was induced by increasing the temperature from 15° C. (at t=0) to 35° C. The concentration of bovine brain tubulin was 2.9 mg/ml and the buffer solution contain 80 mM Pipes, 1 mM MgCl$_2$, 1 mM EGTA, 1 mM GTP, 2.1% DMSO and 10% glycerol at pH 6.9. The black symbols indicate the presence of 0.17 mM glibenclamide whereas the gray symbols represent the controls in its absence. The polymerization was followed simultaneously for one pair at the time, with each pair being a glibenclamide sample and a control, to ensure comparisons are made on identical protein samples. The data presented is representative of four experiments. (b): The rate of tubulin polymerization as measured by the change in OD with time (dOD/dt) as a function of time. The experimental conditions were the same as in (a). Black lines indicate the presence of glibenclamide and gray lines its absence.

Figure 3A:
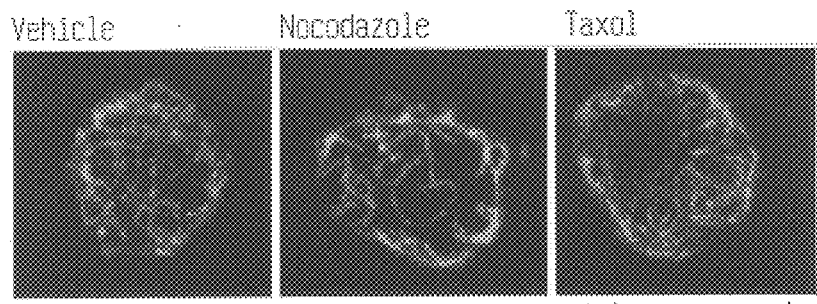
Figure 3B:
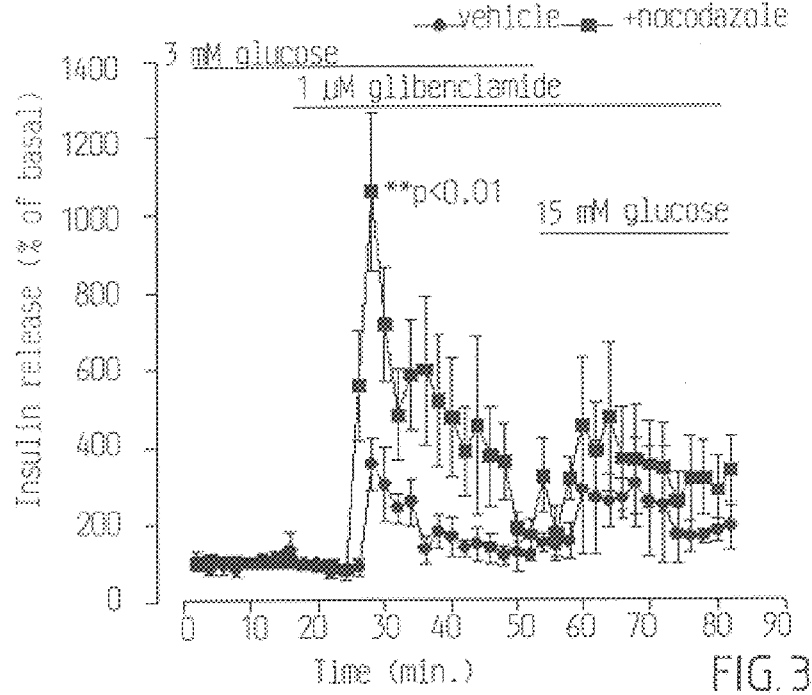
Figure 3C:
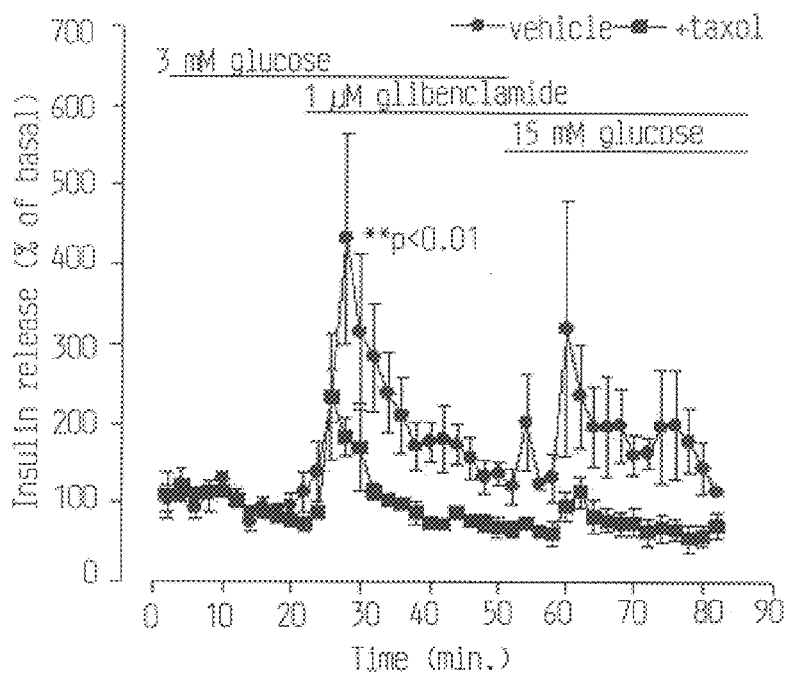

FIGS. 3A, 3B, and 3C

Staining of microtubules with an antibody against tubulin in β-cells pretreated with vehicle, nocodazole or taxol (a). Data are representative of three determinations. Effect of nocodazole (b) and taxol (c) on the dynamics of insulin release from column perifused β-cells. Cells were incubated with 5 µM nocodazole for 30 min or 25 µM taxol for 15 min prior to starting perifusion of the cells. Taxol was present during the whole experiment. The control cells were incubated with their respective vehicle solutions. Protocols were initiated at the times indicated in the figure with either 1 µM glibenclamide or 15 mM glucose. The data represents the mean+SEM of four experiments.

DISCLOSURE OF THE INVENTION

According to the invention β-tubulin, as well as a 65 kDa polypeptide present in pancreatic β-cells, have surprisingly been identified as molecular targets for sulfonylurea compounds. These findings enable for the identification of new insulin secretagogues, which can be sulfonylureas or other compounds acting on these intracellular sulfonylurea targets. The methods according to the invention address a mechanism for insulin secretion, which is independent of the sulfonylurea receptor/K$^+$-ATP complex.

To the inventors' knowledge, there are no indications in the prior art that sulfonylureas interact with tubulin or with the said ~65 kDa polypeptide, which polypeptide as such is an aspect of the invention. Further, it has not been previously shown that compounds which stimulate insulin secretion also have a stimulating effect on tubulin polymerization.

Consequently, in one aspect this invention provides the use of tubulin and/or the ~65 kDa polypeptide, identified according to the Examples below, as targets in the identification of active agents useful for stimulating insulin secretion and thereby useful in the treatment of hyperglycemia and diabetes, in particular NIDDM.

The said active agent could e.g. be a sulfonylurea derivative, or any other compound acting on intracellular targets indicated below. The said active agent could e.g. be a derivative of a "second generation" sulfonylurea, such as glibenclamide (glyburide) or glipizide. In particular, the said active agent should be stimulating insulin secretion independently of the plasma membrane sulfonylurea receptor activity in the presence, but not in the absence, of stimulatory glucose concentrations. As used herein the term "stimulatory glucose concentrations" means a postprandial blood glucose level, such as blood glucose higher than approximately 8 mM.

This invention further provides a method for the identification of a compound capable of binding to the ~65 kDa polypeptide as defined in the Examples below, said method comprising the steps (a) contacting the said ~65 kDa polypeptide with a test compound; and (b) determining the binding of the said test compound to the said ~65 kDa polypeptide. Such a method could include the additional steps of contacting the said ~65 kDa polypeptide with a reference compound binding to the said polypeptide; and determining the binding of the said test compound, relative to that of the said reference compound, to the said ~65 kDa polypeptide.

When the method according to the invention involves the use of a reference compound, the reference compound could be any compound known to bind the 65 kDa polypeptide. It is shown in Example 1, below, that the sulfonylurea glibenclamide (glyburide) is associated with the 65 kDa polypeptide and thus glibenclamide is suitable as a reference compound. It is anticipated that additional suitable reference substances are other sulfonylurea compounds known to stimulate insulin secretion, such as tolbutamide, chlorpropamide, acetohexamide, tolazamide, glimepiride, or a "second generation" sulfonylurea (like glibenclamide) such as glipizide. Sulfonylurea compounds that could be used include those having a generic formula disclosed in e.g. U.S. Pat. Nos. 3,454,635; 3,669,966; or 4,379,785. However, by using the methods according to the invention, the skilled person will be able to identify additional sulfonylurea compounds, sulfonylurea derivatives or other substances, and subsequently use them as reference substances.

In addition, the invention provides a method for the identification of a compound capable of binding to tubulin, comprising the steps (a) contacting tubulin with (i) a test compound and (ii) a reference compound which is a sulfonylurea compound, or a derivative thereof, binding to tubulin; and (b) determining the binding of the said test compound, relative to that of the said reference compound, to tubulin. The said sulfonylurea compound could be any of the sulfonylurea compounds discussed above. As mentioned above, by using the methods according to the invention, the skilled person will be able to identify additional sulfonylurea compounds, sulfonylurea derivatives or other substances, and subsequently use them as reference substances.

In methods described above, binding, in particular a high degree of binding, of the said test compound to the ~65 kDa polypeptide or to tubulin, respectively, is indicative of a compound capable of stimulating insulin secretion.

An alternative method for the identification of a compound capable of binding to tubulin, could comprise the steps (a) contacting tubulin with (i) a test compound and (ii)

a reference compound which is a sulfonylurea compound, or a derivative thereof, binding to tubulin; and (b) determining the stimulating effect of the said test compound, relative to that of the said reference compound, to polymerization or turnover of tubulin. In such a method, a stimulating effect on polymerization or turnover of tubulin is indicative of a compound capable of stimulating insulin secretion.

In the methods described above, the said tubulin could be from any source, but is preferably isolated from humans and in particular human β-cells. Both α-tubulin and β-tubulin consist of various isotypes and there are differences in their tissue distributions (Roach, M. C. et al. (1998) Cell Motility and the Cytoskeleton 39, 273–285; Luduena, R. F. (1993) Mol. Biol. Cell 4:445–457; Luduena, R. F. (1998) Int. Rev. Cytology 178: 207–275). The differences among the β isotypes are known to be conserved in evolution. Since isotypes may differ in their functional assignments or roles in cells, it may be particularly advantageous to use tubulin derived from β-cells when screening for compounds stimulating insulin secretion.

The reference compound could be labeled, e.g. radiolabeled or fluorescence labeled, and binding of the said reference compound to tubulin or the ~65 kDa polypeptide could be determined by methods such autoradiography or fluorescence spectroscopy (e.g. fluorescence polarization, fluorescence correlation spectroscopy, or confocal microscopy (see e.g. Example 1, below)). For a general review on fluorescence spectroscopy methods, see Joseph R. Lakowicz: Principles of fluorescence spectroscopy, Second edition, Kluwer Academic/Plenum Publishers, New York, 1999, ISBN 0-306-46093-9.

The polymerization of tubulin to form microtubules can be followed by a number of methods known in the art, e.g. by observing the increase in optical density of a tubulin solution as described in Example 2, below. There are numerous publications available in which this technique has been used (see e.g. Microtubule Proteins, Editor: Avila, J., 1990, CRC Press). Tubulin polymerization can also be followed using fluorescence labeled tubulin proteins, which upon polymerization end up in close proximity to each other (e.g. quenching or fluorescence resonance energy transfer phenomena). As mentioned above, fluorescence spectroscopy methods are described in the art e.g. by Lakowicz, supra.

Microtubule treadmilling (for a review, see Margolis, R. L. & Wilson, L. (1998) Bioessays 20, 830–836) represents the simultaneous addition of a tubulin heterodimer at one microtubule end and the removal at the other. This phenomenon occurs in living cells and appears to be essential to the biological function of the microtubules (Rodionov, V. I. et al. (1997) Science 275, 215–218). The incorporation of fluorescence labeled tubulin molecules in pre-existing microtubules can thus be utilized in cell-based assays, or alternatively in vitro by fluorescence spectroscopy measurements, e.g. fluorescence anisotropy or correlation spectroscopy, for screening of compounds that via the microtubule network affect secretion of insulin.

In a further aspect, this invention relates to a method for the treatment of diabetes and/or hyperglycemia comprising administering to a patient in need thereof an effective amount of a compound identified by any one of the methods according to the invention. The term "effective amount" means a dosage sufficient to provide treatment for the disease state being treated. The typical daily dose of the active compound varies within a wide range and will depend on various factors such as for example the individual requirement of each patient and the route of administration. In general, daily dosages could be in the range of 0.1 to 1000 mg, such as 1 to 50 mg or 2.5 to 20 mg. It is anticipated that the agents identified by the methods according to the invention could have reduced side effects compared to sulfonylurea compounds known in the art. For a review of the adverse effects and precautions of sulfonylurea drugs, see Paice, B J et al. (1985) Adverse Drug React. Acute Poisoning Rev. 4: 23–36.

In a further important aspect, this invention provides an isolated mammalian polypeptide characterized by binding to glibenclamide and an apparent molecular mass of approximately 65 kDa. In particular, this polypeptide can be identified when the cytosolic fraction of pancreatic β-cells from ob/ob mice is analyzed by SDS-PAGE. However, it will be understood that the invention includes the isolated glibenclamide-binding ~65 kDa polypeptide from any mammalian source.

EXAMPLES

Example 1

Sulfonylureas Associate with 47 kDa and 65 kDa Proteins in β-cell Cytosolic Fractions from ob/ob Mice (a) Binding of Glibenclamide Ob/ob mice were obtained from a locally bread colony at the animal facility within the Karolinska Institute, Stockholm, Sweden. The ob/ob mice were starved overnight. The animals were decapitated, the pancreas was excised from the abdominal cavity and pancreatic β-cells were isolated after collagenase digestion as previously described (Lemmark, A, (1974) Diabetologica 10, 431–438; Nilsson, T. et al. (1987) Biochem. J. 248, 329–336). The cells were kept overnight in RPMI 1640 medium supplemented with 11 mM glucose, 10% FCS, 100 µg/ml streptomycin and 100 IU/ml penicillin at 37° C. in a humidified atmosphere of 5% $CO_2$ in air.

Binding of [$^{125}$I]glibenclamide (Amersham, UK) was performed in intact β-cells and in subcellular fraction derived therefrom. Isolated pancreatic islets from ob/ob mice (250–300) were homogenized in 300 µl buffer containing (in mM): HEPES 20, $MgCl_2$ 1, EGTA 1, EDTA 1, PMSF 1, protease inhibitors (leupeptin, aprotinin, pepstatin, antipain) 0.5 µg/ml in Eppendorf tubes using a motor pestle homogenizer. The homogenized material was centrifuged (800×g for 10 min) and the resultant pellet was resuspended again in 200 µl of homogenization buffer and centrifuged as above. Supernatants from both centrifugations were pooled for high-speed separation (100,000×g for 30 min) of membranes and cytosol. Aliquots were incubated in the presence of 5 nM [$^{125}$I]glibenclamide (2 µCi/sample) with or without ×100 excess of cold glibenclamide. Samples were irradiated for 20 min by 312 nM UV light at room temperature. The reaction was terminated by placing the samples on ice and subjected to SDS-PAGE using standard procedures. Two-dimensional electrophoresis was performed in samples (200 mg protein) to which the following was added: urea powder (final concentration 6 M), isoelectric focusing sample concentrate (33.3% of 3.5–10 ampholine, 16.6% of 2-mercaptoethanol, 33.3% Triton-X 100, 16.6% of 10% SDS). Samples were incubated for 30 min at room temperature and loaded on the gel. After isoelectric focusing (900V, 14 h), the gels were taken out of the tubes, soaked for 30 min at room temperature in Laemmli buffer, and loaded on a 6.6–13.6% gradient gel. Following SDS-PAGE separation, gels were stained with Coomassie Brilliant Blue R or with silver (Silver Stain Plus kit, Bio-Rad, Richmond, Calif.). Localization of the proteins containing the radiolabeled [$^{125}$I]glibenclamide was performed by autoradiography. Binding of [$^{125}$I]glibenclamide to β-cells in suspension isolated from ob/ob mice, followed by UV cross-linking and SDS-PAGE separation was performed to determine whether this compound interacts with cellular proteins other than the SURI unit of $K_{ATP}$-channels. The binding of [$^{125}$I] glibenclamide to β-cells performed under steady-state conditions (30 min at 4° C.) was specific (FIG. 1a), and sub-cellular fractionation revealed that a great proportion of such binding was localized to the plasma membrane, although ~30% of the binding remained associated with the cytosolic fraction. UV cross-linking did not significantly affect either the total binding or its distribution among the cytosolic and membrane fractions (FIG. 1a). This material was further analyzed by SDS-PAGE separation and autoradiography (FIG. 1b). Binding of [$^{125}$I]glibenclamide to β-cells was associated with a ~145 kDa protein within the plasma membrane fraction. In the cytosolic fraction, glibenclamide associated with two proteins having a molecular mass of approximately 47 and 65 kDa, respectively (FIG. 1b, left panel). After several washing steps the binding of [$^{125}$I]glibenclamide remained in the supernatant of the cytosolic fraction for the 65 and 47 kDa proteins (FIG. 1b, middle panel) and in the pellet of the plasma membrane fraction for the 145 kDa protein (FIG. 1b, right panel).

The 145 kDa protein was identified as the regulatory component (SUR-1) of the K$^+$-ATP channel. The identities of the cytosolic proteins were investigated. The cytosolic material was separated using 2-dimensional gel electrophoresis (FIG. 1c), and the proteins were excised for in-gel digestion and MALDI spectrum analysis. The analysis of the 47 kDa protein revealed that it is β-tubulin. Peptides found in the MALDI spectrum (19 of the peptide masses) were applied to the MS-Fit peptide fingerprinting tool. Peptide mass fingerprinting was performed using the MS-Fit algorithm developed at the UCSF Mass Spectrometry Facility and available via http://prospector.ucsf.edu. For the SwissProt database search, the best hit was mouse tubulin β-5 chain (16 matches out of 19), whereas in the NCBI non-redundant database, the best hit was mouse tubulin β-3 chain (17 matches out of 19). The database search for the ~65 kDa protein did not match any known protein sequence.

(b) Confocal Microscopy Analysis

Further analysis of sulfonylureas binding to β-tubulin was performed using confocal microscopy in primary cultures of β-cells obtained from ob/ob mice. Isolated β-cells in culture were incubated in the presence or absence of different agonists for 3 min at 23° C. The incubation time was terminated by fixation of the cells with 4% formaldehyde in PBS for 10 min at room temperature. After rinsing twice with PBS, cells were incubated in acetone at −20° C. for 5 min and then quenched with PBS containing 1% BSA for 30 min. BODIPY® FL glibenclamide was purchased from Molecular Probes, Inc., Catalog Number B-7439; http://www.probes.com). The green-fluorescent BODIPY® FL fluorophore has excitation/emission maxima ~503/512 nm. Staining with BODIPY® FL glibenclamide, primary anti β-tubulin antibody (Amersham, UK) and secondary Texas Red®-conjugated antibody (Molecular Probes Inc.) was performed at room temperature for 1 h. After rinsing with PBS the coverslips were mounted (SlowFade light, Molecular Probes, Eugene, Oreg.) and examined using a confocal laser scanning microscope (Leica TCS NT, Leica Lasertechnik GmbH, Heidelberg, Germany). Excitation wavelengths 488 nm and 568 nm were used. The confocal microscope was equipped with an Ar/Kr laser, a double dicroic mirror for rhodamine/fluorescein and a 63× lens (Leica PL APO 63×/1.32×0.6 oil). Analysis of the data was performed with the IMARIS and COLOCALISATION softwares (Bitplane, Züurich, Switzerland). Co-localization analysis of the data indicated an interaction between glibenclamide and β-tubulin. Interestingly this interaction is mainly localized to the interior of the β-cell and excluded the plasma membrane.

Example 2

Sulfonylureas Affects Tubulin Polymerization in Vitro

To determine whether binding of glibenclamide also occurs in a cell-free system, and whether it has any functional impact on the properties of tubulin, the rate of tubulin polymerization in vitro in the presence of glibenclamide was examined. Polymerization of tubulin leading to the formation of microtubules can be followed by observing the increase in optical density of a tubulin-containing solution at 340 nm. Tubulin polymerization is commonly initiated in vitro either by addition of a crucial buffer component such as GTP or Mg$^{2+}$ (Weisenberg, R. C. (1972) Science 177, 1104–1105) or, alternatively, by an increase in temperature.

Tubulin from bovine brain was purchased from Cytoskeleton Inc. in aliquots of 1 mg lyophilized protein. Glibenclamide was purchased from Sigma and stocks containing 4 mg/ml were prepared daily in dimethylsulfoxide (DMSO). Immediately prior to the microtubule growth experiments each milligram of tubulin was resuspended in 350 μl ice-cold buffer solution (80 mM PIPES, 1 mM MgCl$_2$, 1 mM EGTA and 10% glycerol at pH 6.9) followed by addition of 1 mM ice-cold GTP (Sigma). The samples were mixed and kept on ice for 5 minutes. 170 μl of this solution was subsequently transferred to each of two ice-cold Eppendorff tubes containing 3.65 μl of the glibenclamide stock in DMSO or just DMSO, respectively. Following mixing the solutions were transferred to two cuvettes equilibrated at 15° C. in a CARY 4E spectrophotometer equipped with a thermostated multicell holder. The samples were left in the cuvette holder at 15° C. for five minutes to allow thermal equilibrium to be reached. The experiment was then started by altering the multicell holder set temperature to 35° C. and the absorbance at 340 nm was measured as a function of time. This was done simultaneously for both samples as the multicell holder changes between the two positions. Polymerization started as a result of the increased temperature and the effect of glibenclamide on the rate and extent of polymerization could be observed.

The results are shown in FIG. 2. The rate of change in absorbance was faster in the presence of 0.17 mM glibenclamide and this is the case for three independent pairs of tubulin samples. It has previously been demonstrated that changes in OD are proportional to the concentration of microtubules, regardless of the length of these polymers (Nagle, B. W. & Bryan, J. (1976) Cold Spring Harbor Symposium on Cell Proliferation 3, 1213–1232; MacNeal, R. K. & Purich, D. L. (1978) J. Biol. Chem. 253, 4683–4687). Hence, it is clear from FIG. 2a that although glibenclamide affects the rate of polymerization there is not a strong influence on the extent of polymerization.

Example 3

Taxol Inhibits, and Nocodazole Stimulates, Sulfonylurea Effects on Insulin Secretion Taxol, a promotor of microtubule polymerization, and nocodazole, which induces microtubule depolymerization, have earlier been shown to inhibit glucose-stimulated insulin secretion from isolated rat islets of Langerhans (Howell, S. L. et al. (1982) Bioscience Reports 2, 795–801). Taxol and nodocazole were used to study the functional importance of β-cell microtubules during the process of insulin secretion.

The basal medium used for isolation and for conducting the experiments was a buffer containing 125 mM NaCl; 5.9 mM KCl; 1.3 mM $CaCl_2$; 1.2 mM $MgCl_2$; and 25 mM HEPES (pH 7.4). BSA was added to the medium at the concentration of 1 mg/ml. The dynamics of insulin release were studied by perifusing β-cell aggregates mixed with Bio-Gel P4 polyacrylamide beads (BioRad, Richmond, Calif.), in a 0.5 ml column at 37° C. (Kanatsuna, T. et al. (1981) Diabetes 30, 231–234). The flow rate was 0.2 ml/min. Two-min fractions were collected and insulin content was analyzed by radioimmunoassay.

Cells were incubated with 5 μM nocodazole for 30 min or 25 μM taxol for 15 min prior to starting perifusion of the cells. Taxol was present during the whole experiment. The control cells were incubated with their respective vehicle solutions. Protocols were initiated at the times indicated in FIG. 3 with either 1 μM glibenclamide or 15 mM glucose. The data represent the mean±SEM of four experiments.

Incubation with 5 μM nocodazole and 25 μM Taxol did not affect the basal level of insulin secretion nor did they induce visible changes in the microtubule organization, and the architecture of the β-cells remained intact (FIG. 3a). In the presence of non-stimulating (3 mM) as well as stimulating (15 mM) concentrations of glucose, the presence of 25 μM of Taxol prevented the increase in insulin secretion elicited by 1 μM glibenclamide (FIG. 3c). In contrast, under the same experimental conditions (3 and 15 mM glucose) but in the presence of 5 μM nocodazole, 1 μM glibenclamide induced a 5-fold increase in insulin secretion (at 3 mM glucose) and a one-fold increase at 15 mM glucose (FIG. 3b).

These results suggest that a dynamic microtubule system is required for sulfonylureas to stimulate secretion of insulin. Moreover, they suggest that microtubule dynamics are probably essential for the traffic of insulin containing granules. When taxol, which inhibits tubulin turnover, is present the microtubules are "locked" in place and no more transport can occur. Nocodazole, on the other hand, disrupts microtubules and as such may promote tubulin turnover/treadmilling. This may promote the transport of insulin containing granules to the point of secretion.

Example 4

Characterization of the 65 kDa Polypeptide

Several strategies are employed to determine the identity of the ~65 kDa polypeptide that binds sulfonylureas. Firstly, after sulfonylurea binding to pancreatic β-cell (intact or isolated cytosol) the proteins are separated with 2-dimensional gel electrophoresis. The spot representing the 65 kDa polypeptide binding to glibenclamide is excised and subjected to MALDI analysis.

Additionally, after in vitro binding of sulfonylureas to β-cell cytosol, samples are separated by HPLC and fractions containing the radiolabeled protein separated on SDS-PAGE, and subject to gel staining and autoradiography. The radioactive band will be excised from the gel and sequenced.

What is claimed is:

1. A method for the identification of a compound that bins to β-tubulin, the method comprising:
    (a) contacting β-tubulin with (i) a test compound and (ii) a reference compound comprising a sulfonylurea compound or a derivative thereof that binds to β-tubulin; and
    (b) measuring the binding of the test compound to β-tubulin relative to the binding of the reference compound to β-tubulin, to thereby identify a compound that binds to β-tubulin.

2. The method according to claim 1, further comprising determining whether the test compound stimulates insulin secretion.

3. The method according to claim 1, wherein the sulfonylurea compound is glibenclamide.

4. The method according to claim 1, wherein the β-tubulin is derived from a human source.

5. The method according to claim 1, wherein the test compound stimulates insulin secretion independently of sulfonylurea receptor activity.

6. The method according to claim 1, wherein the test compound stimulates insulin secretion in the presence, but not in the absence, of stimulatory glucose concentrations.

7. A method for identification of a compound that stimulates polymerization or turnover of β-tubulin, the method comprising:
    (a) contacting β-tubulin with a test compound;
    (b) measuring the effect of the test compound on stimulating polymerization or turnover of β-tubulin; and
    (c) determining the effect of the test compound, relative to that of a sulfonylurea compound or a derivative thereof that binds to β-tubulin, on stimulating polymerization or turnover of β-tubulin, to thereby identify a compound that stimulates polymerization or turnover of β-tubulin.

8. The method according to claim 7, wherein the sulfonylurea compound is glibenclamide.

9. The method according to claim 7, wherein the test compound is a sulfonylurea compound or a derivative thereof.

10. The method according to claim 7, wherein the test compound stimulates insulin secretion independently of sulfonylurea receptor activity.

11. The method according to claim 7, wherein the test compound stimulates insulin secretion in the presence, but not in the absence, of stimulatory glucose concentrations.

12. A method for identifying a compound that stimulates insulin secretion, the method comprising:
    (a) contacting β-tubulin with a test compound;
    (b) detecting binding of the test compound to β-tubulin; and
    (c) determining whether the test compound stimulates insulin secretion.

13. The method of claim 12, wherein the test compound is a sulfonylurea compound or a derivative thereof.

14. The method of claim 13, wherein the test compound is glibenclamide.

15. The method of claim 12, further comprising determining whether the test compound stimulates insulin secretion independently of sulfonylurea receptor activity.

16. The method of claim 12, further comprising determining whether the test compound stimulates insulin secretion in the presence, but not in the absence, of stimulatory glucose concentrations.

17. A method for identifying a compound that stimulates insulin secretion, the method comprising:

(a) contacting β-tubulin with a test compound;
(b) detecting stimulation of β-tubulin polymerization or turnover by the test compound; and
(c) determining whether the test compound stimulates insulin secretion.

18. The method of claim 17, wherein the test compound is a sulfonylurea compound or a derivative thereof.

19. The method of claim 18, wherein the test compound is glibenclamide.

20. The method of claim 17, further comprising determining whether the test compound stimulates insulin secretion independently of sulfonylurea receptor activity.

21. The method of claim 17, further comprising determining whether the test compound stimulates insulin secretion in the presence, but not in the absence, of stimulatory glucose concentrations.

* * * * *